United States Patent [19]

Thilly et al.

[11] 4,299,915

[45] Nov. 10, 1981

[54] ASSAY FOR MUTAGENESIS IN BACTERIAL CELLS

[75] Inventors: William G. Thilly, Cambridge, Mass.; Thomas R. Skopek, Stafford Springs, Conn.

[73] Assignee: Massachusetts Institute of Technology, Cambridge, Mass.

[21] Appl. No.: 842,693

[22] Filed: Oct. 17, 1977

[51] Int. Cl.³ .............................................. C12Q 1/68
[52] U.S. Cl. ........................................ 435/6; 435/34; 435/172
[58] Field of Search ................ 195/103.5 R, 103.5 M, 195/78, 79, 112; 435/34, 6

[56] References Cited

U.S. PATENT DOCUMENTS 3,071,518  1/1963  Sherr et al. ........................... 195/79
3,298,923  1/1967  Banno et al. ........................... 195/78
4,072,574  2/1978  Loeb ............................. 195/103.5 R

*Primary Examiner*—Alvin E. Tanenholtz
*Attorney, Agent, or Firm*—Arthur A. Smith, Jr.; David E. Brook

[57] ABSTRACT

An assay is disclosed for determining mutagenic damage caused by the administration of a known or suspected mutagen to bacterial cells such as *Salmonella typhimurium*. After administration of or exposure to a mutagenic agent, the bacterial cells are plated in the presence of a purine analog and resistance to purine analogs is used as the genetic marker. This bioassay system can be used by genetic toxicologists to determine the potential genetic hazards from the use of a variety of suspected or known mutagens, including newly-developed chemicals.

1 Claim, 10 Drawing Figures

ASSAY FOR MUTAGENESIS IN BACTERIAL CELLS

GOVERNMENT SPONSORSHIP

Work relating to this invention is partially supported by grants from the National Institutes of Health. Specifically, these grants were N.C.I. 5-R01-CA 15010 from the National Cancer Institute; N.I.E.H.S. 2-P01-ES00597 from the National Institute of Environmental Sciences; and NIH 1-T32-ES07020 from the National Institute of Health.

BACKGROUND OF THE INVENTION

1. Field of the Invention

This invention is in the field of biochemistry and more specifically relates to genetic toxicology.

2. Description of the Prior Art

Compounds or other agents which can chemically alter the DNA of a cell are capable of inducing genetic diseases such as Lesch-Nyhan syndrone, hemophilia, sickle cell anemia, and cystic fibrosis. Compounds or agents having this potential are known as mutagens. In addition, most mutagens also have the capability of inducing cancer in test animals. Clearly, it is desirable to have methods for determining the potential mutagenicity of such agents in a practical manner, and bacterial mutation assays have been proposed for this reason.

One of the most commonly used bacterial assays for mutagenicity is known as the Ames assay and employs a set of *Salmonella typhimurium* strains which are permeable to a wide range of chemicals and also are partially deficient in DNA repair. Ames, B. N., McCann, J. and Yamasaki, E. *Mutation Research* 31, 347-379 (1975). In this system, a chemical's mutagenicity is determined by ability to revert a set of histidine-requiring mutants of *S. typhimurium* back to histidine prototrophy through reverse mutation of the original DNA lesion or through a second site mutation. While the Ames assay is a valuable genetic tool, its basic design makes it undesirable for screening purposes. This is because the Ames assay is a reverse mutation assay in which a mutant DNA locus must be specifically mutated back to its wild-type configuration or suppressed. A chemical mutagen which cannot affect the required change in the DNA will go undetected. Such mutagen specificity is known, of course.

Because of the problems with reverse assays, it would be desirable to provide a forward mutation assay based upon the inability of bacterial cells to enzymatically convert a drug to a toxic metabolite. In such an assay, a large portion of a structural gene serves as the target for the chemical mutagen. Base-pair substitutions affecting amino acids at the catalytic site or at key structural positions would be observed as a phenotypic change to drug-resistance. Frameshifts occurring over most of the structural gene, except perhaps the terminal codon sequences, would similarly be expressed. With such advantages in mind, forward mutation assays based on drug-resistance have been proposed for bacterial cells.

For example, Ellenberger and Mohn have developed a forward mutation assay based on 5-methyltryptophan in *E. coli*. See Ellenberger, J. and Mohn, G., *Arch. Toxicol.* 33, 225 (1975). Forward mutations leading to 5-methyltryptophan resistance are known to occur in five different genes. This sytem has been shown to respond to a variety of mutagens. There are some serious practical problems with the assay, however. Varying the concentration of 5-methyltryptophan changes the observed mutant fraction. Also, 5-methyltryptophan-sensitive bacteria are not completely inhibited by 5-methyltryptophan and continue to grow slowly in its presence on the plate. See Mohn, G., *Mut. Res.* 20, 7 (1973). This complicates the quantitation of mutation.

SUMMARY OF THE INVENTION

This invention relates to a new assay for determining mutagenesis in bacterial cell cultures.

More specifically, the assay involves the exposure of a culture of bacterial cells, such as *S. typhimurium*, to an agent to be tested for its mutagenic effects. The exposed cells are then plated in the presence of a purine analog, such as 8-azaguanine. Mutant cells lacking the enzymes which convert the purine analog to its toxic metabolite grow to form macroscopic colonies and are counted. Cells are plated under conditions which allow a sufficient number of cell divisions to occur for full phenotypic expression of the mutation.

The degree of mutagenesis can be determined by calculating the fraction of analog-resistant mutant cells in the treated population or by other techniques. By administering different dosages of the suspected mutagen, dose-response relationships can be established.

Metabolizing systems can also be added to the bacterial cell cultures to determine whether any metabolite by-products of a tested compound are mutagens.

The assay procedure described herein was significant advantages over those previously known. It provides a simple, quick, and inexpensive means for determining the mutagenicity of compounds or other agents. Because it is a forward assay, it is more reliable and more likely to detect most potential mutagens than reversion assays.

DESCRIPTION OF PREFERRED EMBODIMENTS

Figure 1:
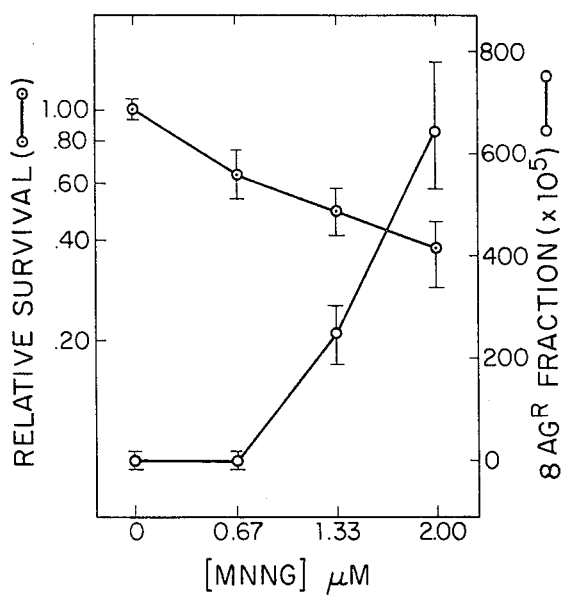
FIGS. 1-7 are plots illustrating the concentration-dependent toxicity and mutagenicity of various mutagens tested in the assay of this invention, some having comparative data obtained using the Ames reversion assay.
Figure 2:
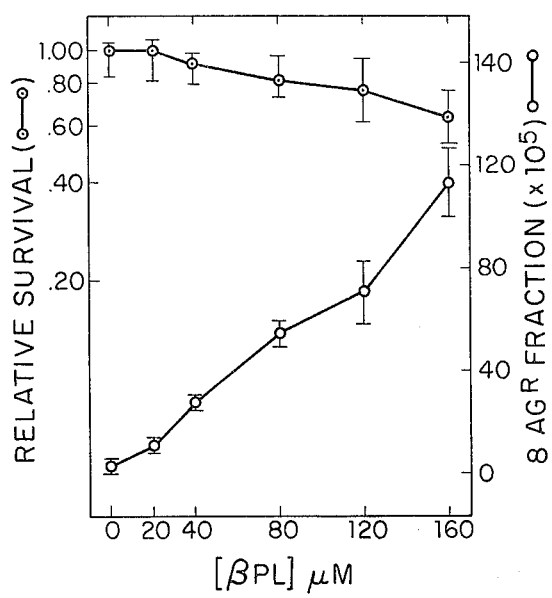
Figure 3:
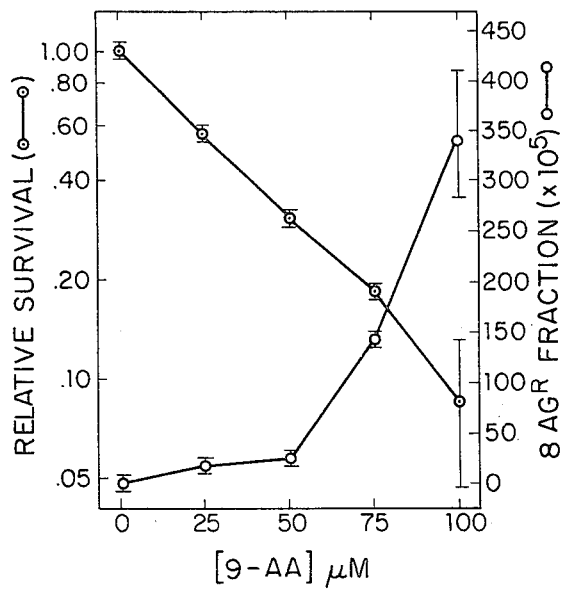
Figure 4:
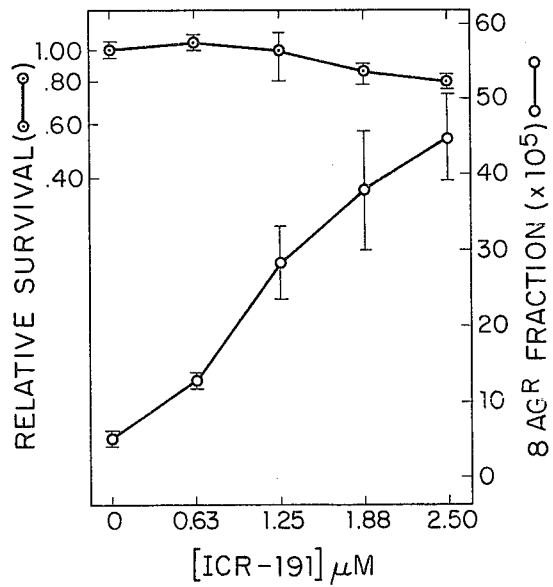

The bacteria used in most of the actual experimental work described herein was bacterial strain TM35 which is a spontaneous histidine prototrophic revertant of *S. typhimurium* strain TA1535. Strain TM35 originated from a clone chosen randomly from spontaneous revertant colonies isolated on a minimal E agar plate containing 0.05 mM biotin without histidine. *S. typhimurium* strain TM677 was also used. TM677 was derived from TM35 and contains the plasmid poKM101 which was transferred conjugatively from *S. typhimurium* strain TA2000. Other bacterial cells which are sensitive to purine analogues could also be used. Specific examples of additional suitable bacterial strains are: *E. coli, B. subtilis, S. fecalis*, and other Salmonella strains. Those skilled in the art will know, or will be able to ascertain using no more than routine experimentation, other suitable bacterial strains for use in the assay described herein.

The initial step in the mutagenesis assay is the exposure of a culture of bacterial cells to a suspected or known mutagen. In the case of chemical mutagens, these can simply be added to the culture suspension. Physical agents, such as electromagnetic or nuclear radiation, can also be used. For example, a culture of growing bacterial cells can be irradiated with ultraviolet light to test for mutagenesis. Other conditions, such as heat, cold, or exposure to other microorganisms, such as viruses, can also be used to cause mutagenesis.

It is desirable to establish exponential cell growth prior to exposure to mutagen. The dosage of mutagen, exposure time, etc., can vary widely. It is believed that any dosage and/or exposure can be used as long as some fraction of the treated bacterial cells survive. To check this, the cells are resuspended after exposure to the mutagen in fresh medium and the surviving fraction is determined by plating. In cases where the mutagen being tested is exceptionally cytotoxic, it may be necessary to use more cells initially. In a typical assay, the cells are exposed to a suspected chemical mutagen for about 2 hours, but there is nothing critical about this time and wide variations are possible.

The cells can be plated immediately after treatment with the mutagen. It appears that the amount of residual growth that occurs on the plates is sufficient for full phenotypic expression, even when cultures are plated immediately after treatment. In fact, the mutant fraction drops significantly and then stabilizes at a constant level when the cultures are allowed to grow before plating. This is a phenomenon probably resulting from the fact that rapidly growing bacteria possess multiple copies of their DNA. See Cooper, S. and Helmstetter, C. E., *J. Mol. Biol.* 31, 519–540 (1968).

The pH of the plate used to select mutants has been found to be a very important parameter. As is known, the reaction rate of enzymes, including purine phosphoribosyl transferases varies with pH. Additionally, the pH effects the rate of bacterial growth.

In general, the pH of the plate on which mutant cells are selected should be within a range which allows the reaction between the enzyme and substrate to proceed rapidly enough to inhibit wild-type-cell growth, but not so rapidly that the bacterial cells are stopped before expressing their phenotypically-developed resistance to the purine analogue. Generally, this requires at least ten cell divisions.

More specifically, in the case of *S. typhimurium* strain and 8-azaguanine, the operable pH range is from about 5.0 to about 8.0, whereas the preferred pH range is between about 6.0 and about 6.5.

In the experiments described herein, the bacterial cells have been suspended in Brain Heart Infusion medium. In addition, any culture medium is suitable as long as it allows good bacterial cell growth. Among other known media considered to be suitable are: nutrient broth (Difco), Earle's minimal medium, M-9 medium (Difco).

Resistance to purine analogs, such as 8-azaguanine, is used as the genetic marker. Resistance to purine analogs is apparently related to the mutational loss or modification of the purine phosphoribosyl transferases in the cell. These are enzymes which transport purines and purine analogs into the cell and phosphoribosylate them. 8-azaguanine was the purine analogue used in the experiments described herein. Nevertheless, other purines or purine analogues could also be incubated with the treated cells. Specific additional examples are 6-mercaptopurine, 2,6-diaminopurine, 8-azaxanthine, 6-thioguanine and 8-azahypoxanthine. Those skilled in the art will known, or be able to ascertain using no more than routine experimentation, other suitable purine phosphoribosyl transferase substrates.

The treated bacteria were plated in agar plates containing the purine analog to determine the mutant fraction in the experiments described herein. Other methods, such as serial dilution of the treated population and growth in liquid culture containing the purine analog, could also be used. Those skilled in the art are familiar with such techniques.

It is often desirable to add an active drug-metabolizing system to mutagenesis assay systems to help in interpreting negative results. This is because the enzyme systems represented by the cell microsomes often catalyze chemical reactions producing genetically active derivatives from inactive precursors. In assays such as that described herein, the bacterial cells grow rapidly in culture and do not express significant drug-metabolizing activity. The addition of an active drug-metabolizing system to these cell cultures, therefore, makes a more complete bioassay system.

One known metabolizing system is formed from a dulute liver post-mitrochondrial supernatant (PMS) obtained from rats previously treated with phenobarbital or methylcholanthrene. Ames, B. N., Mutagenic Effects of Environmental Contaminants, eds. Sutton, H. E. and Harris, M. I., 57–66, Academic Press, N. Y. (1972). Those skilled in the art will know or be able to ascertain others, using no more than routine experimentation.

An active, drug-metabolizing system particularly suitable for use in the mutagenesis assays described herein, or in other bioassays, can be prepared as follows. In the first step, mammalian tissue, such as rat liver tissue, is homogenized in an aqueous suspension medium. Relatively large cellular particles are removed to produce a post-mitochondrial supernatant (PMS). The PMS supernatant is usually not free of contamination, but this can be removed by filtering the PMS through a filter having an appropriate pore size.

There are many possible suitable sources of mammalian tissue, with rat liver being one which is commonly used. For assays of human mutagenesis potential, it is preferred, of course, to use active human tissue enzymes such as might be obtained from human liver tissue. Homogenization can be performed by any of the known techniques usually employing homogenizers which are designed for just this purpose. The relatively large particles, or mitochondria, can be removed by centrifuging the homogenized material to produce a supernatant fraction of PMS. This serves as a source of microsomal enzyme. After removal of the mitochondria, the supernatant is filtered through filters having a pore size sufficient to remove contaminating bacteria, and preferably between about 0.22 and about 3 microns.

A particularly preferred drug metabolizing system can be created by adding between about 0.25 grams and about one micromole per milliliter (mm/ml) of nicotinamide adenine dinucleotide, oxidized form (NADH).

Other techniques can be used to provide the desired metabolizing capability to the bioassays. It has been demonstrated, for example, that target cells can be cocultivated with primary cell populations capable of drug metabolism. Marguardt, H. and Heidelberger, C., *Cancer Res.*, 32, 721–725 (1972).

EXAMPLE 1

ASSAY FOR MUTATION IN BACTERIAL CELLS BY KNOWN MUTAGENS

The bacterial strains used in the forward assay of this invention were strains TM35 and TM677. In the Ames reversion assays, the strains used were TA1535, TA100, TA1538, TA98 and TA b 1537.

Cells were grown in Brain Heart Infusion (Difco) at 37° C. to a density of approximately $8 \times 10^8$/ml and then divided into 0.5 ml aliquots. Each aliquot received 55.5 $\mu$l dimethyl sulfoxide (DMSO) and was then immediately frozen and stored at $-80°$ C. Upon thawing, each frozen aliquot contained approximately $1.25 \times 10^8$ viable cells. The use of identical frozen aliquots is an important contributor to reproducibility among experiments performed on different days. For each mutation experiment two frozen aliquots of TM35 were quickly thawed in a 37° C. water bath and added to 49 ml of Minimal E medium (0.2 mg/ml MgSO$_4$·7H$_2$O, 2.0 mg/ml citric acid·H$_2$O, 10 mg/mk K$_2$HPO$_4$, 3.5 mg/ml NaNH$_4$HPO$_4$·4H$_2$O, 20.0 mg/ml glucose, 0.05 mM biltin; pH7.0) in a 100 ml screw-cap bottle. The culture was incubated for one hour at 37° C. in a shaking water bath (200 RPM). Doubling time was approximately 40 minutes.

For compounds not requiring metabolic activation, 4.95 ml samples of the culture were then placed in 20 ml screw cap vials. The test compound was delivered to each vial in 50 $\mu$l DMSO. The vials were returned to the shaking 37° C. water bath and incubated for 2 hrs.

For compounds requiring metabolic activation, four ml samples of the culture were placed in 25 cm$^2$ plastic tissue culture flasks (Falcon). Each flask then received 0.5 and sterile post-mitochondria, supernatant (PMS), 2 units glucose-6-phosphate dehydrogenase (delivered in 50 $\mu$l 5 mM citrate), and 0.5 ml Minimal E containing 5 mg G6P, 5 mg NADP+, and 33.5 mg MgCl$_2$. Controls with no PMS9 received 0.5 ml PBS and 0.5 ml Minimal E instead of the PMS9 and cofactors, respectively. The flasks were then placed in a 37° C. dry-air incubator and incubated for 1 to 3 hours.

After the treatment period, the cultures were transferred to plastic centrifuge tubes (Falcon) and centrifuged at 2000 RPM for 15 min. The cultures were resuspended at room temperature in phosphate buffered saline (PBS) (1.0 mg/mk NaCl, 0.2 mg/ml KCl, 1.15 mg/ml Na$_2$HPO$_4$, 0.2 mg/ml KH$_2$PO$_4$; pH7.0) and diluted to a cell concentration of $1.0 \times 10^7$/ml.

To determine the number of 8AG$^R$ cells in each sample, 0.4 ml of the PBS dilution and 175 $\mu$l of a 20 mg/ml solution of 8AG in DMSO were added to 9.5 ml liquid (42° C.) top agar (0.6% Difco agar, 0.6% NaCl, 0.05 mM biotin). 2.5 ml of this mixture was then layered over each of three 100 mm plastic petri dishes (Fisher) containing 15 ml Minimal E medium (pH6.5) solidified with 0.6% agar. Therefore, about $1 \times 10^6$ cells were plated in each dish with a final 8AG concentration of 50 $\mu$g/ml.

To determine toxicity and, hence, the number of viable cells on the 8AG plates, a $10^{-4}$ dilution was made of the original PBS dilution and 0.5 ml of this was added to 3.6 ml liquid top agar. One ml of the mixture was then layered over each of three 60 mm petri dishes (Fisher) containing 8 ml Minimal E medium (pH6.5) solidified with 0.6% agar.

Clones arising on the mutation and toxicity plates were counted by an automatic colony counter (Artek Systems) after 36 hours incubation at 37° C. in a dry air incubator. The fraction of 8AG$^R$ mutants following treatment is calculated as follows: 8AG$^R$ Fraction = [number of clones on 8AG containing plates)/(number of clones on plates without 8AG)] ($10^{-4}$).

The dose-dependent toxicity and mutagenicity of N-methyl-N'-nitro-N-nitrosogunanidine (MNNG), substituted chlorinated acridine (ICR-191), 9-aminoacridine (9AA) and $\beta$-propiolactone ($\beta$PL) in 2 hour exposures are shown in FIGS. 1–4. All four compounds, at relatively low concentrations, induced mutant fractions (M.F.) significantly higher than background levels.

Figure 5:
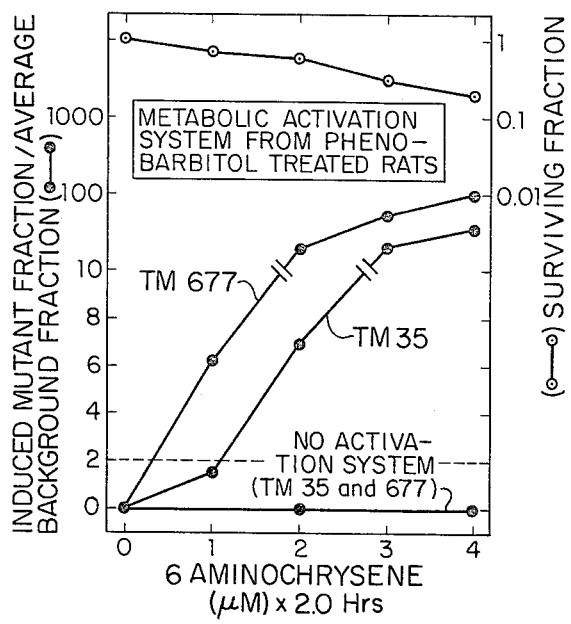

FIG. 5 presents a plot of data obtained for 6-aminochrysene for strains TM35 and TM677.

Figure 6:
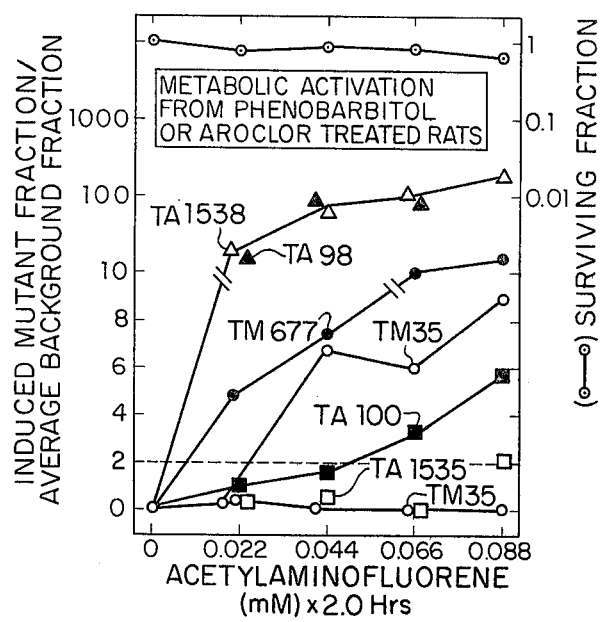
Figure 7:
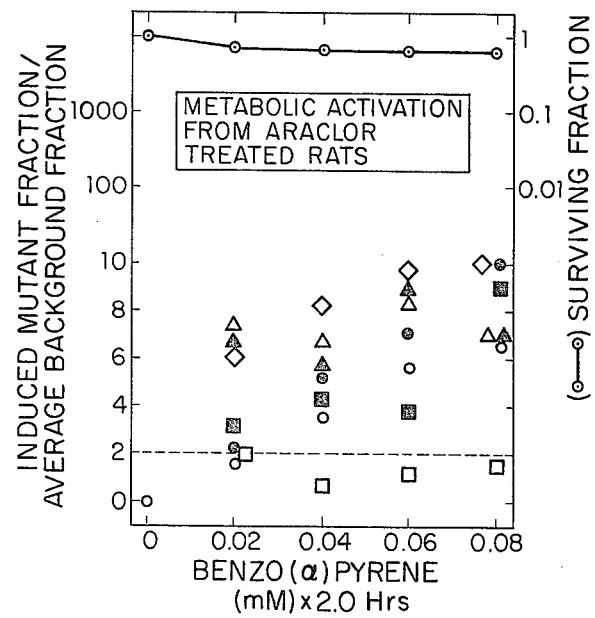
Figure 8:
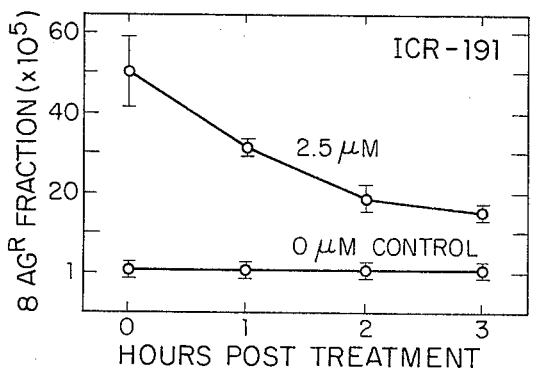
FIGS. 8 and 9 are plots illustrating the decrease in mutant fraction during cell grow-back as a function of time-after-treatment in forward assays according to this invention; and, FIG. 10 is a plot illustrating decrease in mutant fraction as a function of time-after-treatment in an Ames reversion assay.

FIGS. 6 and 7 present comparative data between forward assays of this invention and Ames reversion assays for nitrosamine, acetylaminofluorene and benzo($\alpha$)pyrene, respectively. The bacterial strains used in the Ames reversion assays were TA1535, TA100, TA1538, TA98 and TA1537. In the Ames assay, culture inoculation, growth and treatment were similar to those described for the forward assays except that: (1) 5mM histidine was added to the Minimal E growth medium; and (2) cell density at the beginning of treatment was $1 \times 10^8$/ml. After treatment, the cells were centrifuged, washed in 5 ml PBS, centrifuged again and resuspended in 0.5 ml PBS. 0.1 ml of this was then plated on each of three Minimal E agar plates with biotin and no histidine (mutation plates). 0.1 ml of a $10^{-6}$ dilution of the PBS suspension was plated on each of three Minimal E agar plates containing biotin and 5 mM histidine (toxicity plates).

Toxicity data presented in FIGS. 5–8 are for all points.

EXAMPLE 2

PHENOTYPIC EXPRESSION

Figure 10:
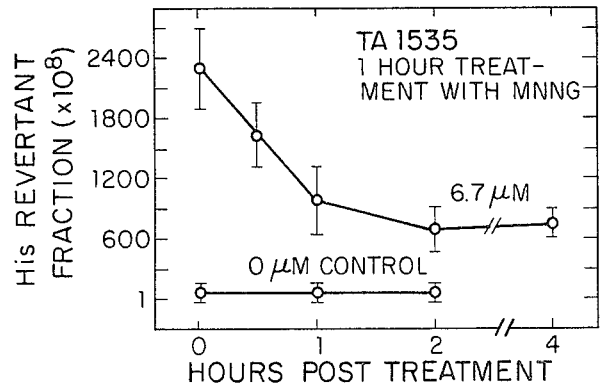
Figure 9:
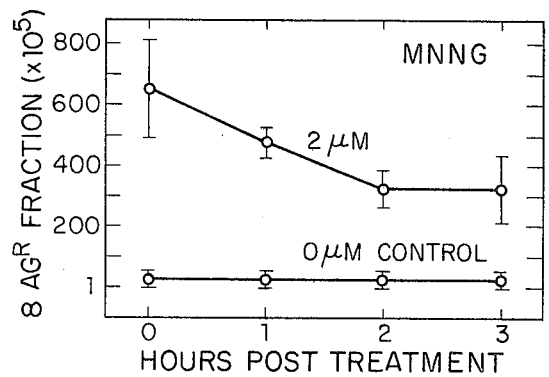

The assay procedure of Example 1 was used and cells were plated under selective conditions within 30 minutes after treatment with the mutagen. Cultures were grown in Minimal E post-treatment to ascertain the time required for full phenotypic expression of the mutation. Treatment procedure was the same as described above. After treatment with ICR-191 or MNNG, cultures were incubated in Minimal E, and hourly samples were plated to determine 8-azaguanine resistant (8AG$^R$) mutant fraction. The data from this experiment is presented in FIGS. 9 and 10. It appears that the amount of residual growth that occurs on the 8AG plates is sufficient for full phenotypic expression, even when the cultures are plated immediately after treatment. In fact, the mutant fraction drops significantly and then stabilizes at a constant level when the cultures are allowed to grow before plating. This phenomenon probably results from the fact that rapidly growing bacteria possess multiple copies of their DNA. A mutation in one of the copies of the SGPRT locus present in a given bacterium will be "diluted out" if the bacterium is allowed to divide instead of being plated immediately. This would account for the fall in mutant fraction.

FIG. 11 presents data from a similar experiment using the Ames' reversion assay. Treatment and plating procedures have been described in the literature. DeLuca, J. G., Krolewski, J. J., Skopek, T. R., Kaden, D. A. and Thilly, W. G., *Mutation Research* (in press), (1977)). The same drop in mutant fraction during grow-back post-treatment can be seen in this system as well.

EXAMPLE 3

Fluctuation Test

In order to test the hypothesis that $8AG^R$ mutants arise spontaneously by a process independent of the application of selective conditions, the fluctuation test of Luria and Delbruck was performed. Luria, S. E. and Delbruck, M. *Genetics* 28, 491–511 (1943). An $8AG^S$ culture (TM35, $3\times 10^6$/ml) was sampled and plated in quintuplicate to determine the $8AG^R$ background fraction. The culture was then diluted $10^6$-fold with Minimal E medium and 15 independent 1 ml cultures were initiated (~3 cells per culture). These were allowed to grow for 36 hr at 37° C. Each culture was then diluted to $10^7$/ml and plated in triplicate to determine the $8AG^R$ fraction. Analysis of variance (ANOVA) was performed to compare the variation among replicate samples from the original culture and the variation among the 15 subcultures. ANOVA showed that the variation in the $8AG^R$ fraction among different samples taken from the original population was the same as the variation associated with the determination of each mutant fraction (p=0.2). However, the variation in the $8AG^R$ fraction among the 15 subcultures initiated from small inocula was significantly different from the variation associated with the determination of each mutant fraction (p <<0.01). These data indicate that resistance to 8AG results from a random mutational event.

EXAMPLE 4

UPTAKE OF TAGGED 8AG BY $8AG^S$ AND $8AG^R$ CELLS

In order to begin the biochemical characterization of the mutation assay, the ability of $8AG^R$ and $8AG^S$ cells to take up radioactive 8AG was compared. Twenty-five $8AG^R$ and mutant clones were isolated from 8AG containing plates, purified and stored in frozen aliquots as described in Example 1. Five were spontaneous mutants; 5 each were induced by ICR-191, 9AA, MNNG, and βPL. A 0.45 ml Minimal E culture of each mutant strain and a wild-type control was prepared (~1 $1\times 10^8$cells/ml). After a 1 hr preincubation at 37° C., 0.01 μmoles[$^{14}$C]8AG (22 μmole) was delivered to each culture in 50 μl 0.01 N NaOH. A 0.2 ml sample was taken from each at the time of [$^{14}$C]8AG addition and again after 2 hr incubation at 37° C. Each 0.2 ml sample was filtered through a 0.45 μ Millipore filter and quickly washed with 50 ml PBS. The filters were dried, added to 10 ml Aquasol (New England Nuclear) and counted in a liquid scintillation counter.

The [$^{14}$C]8AG incorporation rates of the 25 $8AG^R$ mutants expressed as % of the wild-type control, are presented in Table 1.

TABLE 1

| 8AG INCORPORATION RATE OF $8AG^R$ MUTANTS | | | |
|---|---|---|---|
| Mutant | 8AG Inc. (% wild-type) | Mutant | 8AG Inc. (% wild-type) |
| S-1 | 2.4 | BPL-4 | 1.8 |
| S-2 | 1.7 | BPL-5 | 1.2 |
| S-3 | 18.3 | 9AA-1 | <0.04 |
| S-4 | 5.9 | 9AA-2 | <0.04 |
| S-5 | 19.5 | 9AA-3 | <0.04 |
| NG-1 | 0.04 | 9AA-4 | <0.04 |
| NG-2 | 5.1 | 9AA-5 | <0.04 |
| NG-3 | 2.2 | ICR-1 | <0.04 |
| NG-4 | 4.9 | ICR-2 | <0.04 |
| NG-5 | 3.2 | ICR-3 | 0.80 |
| BPL-1 | 0.1 | ICR-4 | <0.04 |
| BPL-2 | 2.5 | ICR-5 | 11.8 |
| BPL-3 | 7.1 | | |

S mutants are spontaneous $8AG^R$ mutants; NG mutants were induced by MNNG; BPL mutants were induced by βPL; 9AA mutants were induced by 9AA; ICR mutants were induced by ICR-191.

The 8AG incorporation rate of the wild-type control was $5\times 10^{-18}$ moles/cell-hr. Uptake of [$^{14}$C]AG in the control was linear through the 2 hr incubation, and the concentration of 8AG used was saturating. Of the mutants tested, 9 had no detectable (<0.04%) activity, while the other 16 possessed partial activity (0.1% to 19.5%).

EXAMPLE 5

Reconstruction Experiments

In order to test for possible bias in quantitative determination of induced $8AG^R$ mutation, 2 reconstruction experiments were performed. In the first, the plating efficiency of 5 spontaneous $8AG^R$ mutants in the presence of 8AG and $8AG^S$ cells was determined. Each $8AG^R$ mutant was subjected to 3 plating conditions: (1) 0 μg/ml 8AG; (2) 50 μg/ml 8AG; and (3) 50 μg/ml 8AG plus $1\times 10^6$ $8AG^S$ cells/plate. The results of this experiment are shown in Table 2.

TABLE 2

| PLATING EFFICIENCY OF $8AG^R$ CLONES IN THE PRESENCE OF 8AG AND $8AG^S$ CELLS | | | |
|---|---|---|---|
| | Control | 8AG | 8AG w/cells |
| S-1 | 1.00 ± .15 | 0.93 ± .05 | 0.8 ± .07 |
| S-2 | 1.00 ± .02 | 1.16 ± .03 | 1.04 ± .03 |
| S-3 | 1.00 ± .04 | 0.95 ± .03 | 0.87 ± .08* |
| S-4 | 1.00 ± .07 | 0.98 ± .01 | 0.83 ± .03* |
| S-5 | 1.00 ± .08 | 0.92 ± .01 | 0.73 ± .08* |

S-1, S-2, S-3, S-4, S-5 are randomly chosen spontaneous $8AG^R$ clones, plated on Minimal E agar (control), with 50 ug/ml 8AG (8AG), or with 50 ug/ml 8AG plus $10^6$ $8AG^S$ cells (8AG w/cells).
Values shown are ± standart deviation.
*t-test shows these values to be statistically less then control (p < .05).

8AG alone had no effect; however, the presence of 8AG with $8AG^S$ cells did decrease plating efficiency slightly. This might be the result of cross-feeding of toxic product between $8AG^S$ and $8AG^R$ cells.

In the second reconstruction experiment a population containing a known high fraction of $8AG^R$ cells was exposed to the exact protocol of the mutation assay to test for any possible quantitative effect of the protocol on the differential ability of $8AG^R$ and $8AG^S$ cells to grow and form colonies. A mixed population of $8AG^S$ and $8AG^R$ cells was prepared (1 $8AG^R$ cell: 2 $8AG^S$ cells). This population was treated for 2 hr with 0, 0.16, and 1.60 mM βPL. After treatment and resuspension in PBS, the culture was diluted and plated with and without 8AG to determine the relative survival of the mixed population and the ratio of $8AG^R$ to $8AG^S$ cells. The experiment was performed twice with two different spontaneous $8AG^R$ mutants. The results are presented in Table 3. The high concentration of βPL killed a significant portion of the mixed population. However, the ratio of $8AG^R$ cells to $8AG^S$ cells in the treated population did not suffer significantly, indicating that there is no appreciable systemic bias in the quantitative determination of induced mutant fraction.

Those skilled in the art will recognize many equivalents to the specific embodiments of the invention described herein. Such equivalents are considered part of this invention and are intended to be encompassed by the scope of the following claims.

What is claimed is:

1. An assay for determining mutagenesis, comprising:
   a. exposing a culture of bacterial cells to an agent to be tested for its mutagenic effects on said cells and then adding an active drug-metabolizing system to said culture of bacterial cells;
   b. incubating exposed cells in the presence of a purine analog which acts as a purine phosphoribosyl transferase substrate and under conditions which allow said exposed cells to express phenotypically-developed resistance to said purine analog; and,
   c. determining the fraction of mutant cells.